(12) United States Patent
Watanabe et al.

(10) Patent No.: US 9,207,218 B2
(45) Date of Patent: Dec. 8, 2015

(54) CAPILLARY COLUMN

(71) Applicant: Frontier Laboratories, Ltd., Koriyama-shi, Fukushima (JP)

(72) Inventors: Chuichi Watanabe, Fukushima (JP); Koichi Ito, Fukushima (JP); Atsushi Watanabe, Fukushima (JP)

(73) Assignee: FRONTIER LABORATORIES LTD., Fukushima (JP)

( * ) Notice: Subject to any disclaimer, the term of this patent is extended or adjusted under 35 U.S.C. 154(b) by 50 days.

(21) Appl. No.: 14/109,867

(22) Filed: Dec. 17, 2013

(65) Prior Publication Data

US 2014/0165840 A1 Jun. 19, 2014

(30) Foreign Application Priority Data

Dec. 19, 2012 (JP) ................. 2012-277104

(51) Int. Cl.
*G01N 30/60* (2006.01)
*G01N 30/02* (2006.01)

(52) U.S. Cl.
CPC ........ *G01N 30/6078* (2013.01); *G01N 30/6086* (2013.01); *G01N 2030/025* (2013.01)

(58) Field of Classification Search
CPC .......... G01N 30/6073; G01N 30/6078; G01N 30/6086
USPC ....................................... 73/23.39
See application file for complete search history.

(56) References Cited

U.S. PATENT DOCUMENTS

2006/0027098 A1* 2/2006 Lautamo ................... 95/82

FOREIGN PATENT DOCUMENTS

JP 2006-177917 7/2006

OTHER PUBLICATIONS

D.H. Desty, "The Origination, Development and Potentialities of Glass Capillary Columns", Chromatographia, vol. 8, No. 9, Sep. 1975, pp. 452-455.*
D.H. Desty et al., "Non-Circular Capillary Columns for Gas Chromatography", Journal of Chromatography, 142 (1977), pp. 39-56.*
H. D. Papendick and J. Baudisch, "Tapeworm Columns in Gas Chromatography," Journal of Chromatography, vol. 122, pp. 443-450, Jul. 1976.
P. Sandra et al., "Experiments with Capillary Columns Having Unconventional Cross-Sectional Geometry", Journal of HRC & CC, vol. 3, pp. 253-256 (May 1980).

* cited by examiner

*Primary Examiner* — Robert Clemente
(74) *Attorney, Agent, or Firm* — Paul A. Guss (57) ABSTRACT

There is provided a capillary column comprising a flat cross section and a desired theoretical plate number and having both high resolution and high sample load capacity. The capillary column 1 comprising a stationary phase on an inactivated inner surface, which is used in gas chromatography, comprises a narrow part 3 formed in a central part of a cross section of internal space and a bulge part 4 formed on each of both sides of the narrow part 3.

7 Claims, 6 Drawing Sheets

CAPILLARY COLUMN

BACKGROUND OF THE INVENTION

1. Field of the Invention

The present invention relates to a capillary column used in gas chromatography.

2. Description of the Related Art

A capillary column for gas chromatography generally has a circular-shaped cross section, and it is theoretically known that when the length of a column is the same, higher resolution can be obtained by narrowing the inside diameter of the column. For example, a capillary column having a circular-shaped cross section (hereinafter abbreviated as "circular capillary column") having the minimum diameter among the circular capillary columns available at present has an inside diameter of 0.1 mm, has a high theoretical plate number of 9000 plates/m (p/m), and can obtain high resolution. However, a problem of a circular capillary column having an inside diameter of 0.1 mm is that sufficient sample load capacity cannot be obtained.

Note that, in the present application, the "sample load capacity" of a certain capillary column means the maximum sample capacity at which peaks of sharp identical shape can be obtained when the capillary column is used in gas chromatography. That is, as the sample load capacity becomes larger, gas chromatography can be performed without diluting or dividing a sample, and thereby the detection sensitivity of minor components is also advantageously improved. Here, the "sample load capacity" of a certain capillary column is represented by the ratio to the sample load capacity of a circular capillary column having an inside diameter corresponding to the maximum width of the inside dimension in the thickness direction of the capillary column.

On the other hand, in contrast to the circular capillary column, a theory is proposed that a higher resolution than that of the circular capillary column can be obtained by changing the shape of the cross section to a rectangular shape (refer to H. D. Papendick et al., J. Chromatogr., 122, 443-450 (1978)). Here, if the inner peripheral length of the rectangular cross section is the same as the inner peripheral length of the circular capillary column, a capillary column having a rectangular cross section will be able to obtain higher sample load capacity as compared with the circular capillary column and thus have both high resolution and high sample load capacity.

However, the above theory has only showed the superiority of the capillary column having a rectangular cross section over the circular capillary column by a mathematical expression and the capillary column having a rectangular cross section has not been realized.

On the other hand, a capillary column having a rectangular cross section has also been proposed (for example, refer to Japanese Patent Laid-Open No. 2006-177917). The above conventional capillary column having a rectangular cross section is prepared by opposing two partition walls each made of a stainless steel sheet having a thickness of 0.2 mm and a width of 100 mm, disposing stainless steel sheets each having a thickness of 0.2 mm and a width of 5 mm at both ends of the partition walls as a spacer, brazing the spacers to the partition walls, and applying a material serving as a stationary phase to an inner surface of the capillary column. Alternatively, the capillary column may be prepared by applying the material serving as a stationary phase to the inner surface of the partition walls and then bonding or soldering both ends of the two opposed partition walls.

However, it is difficult to produce the capillary column having a rectangular cross section as a long capillary column up to tens of meters, and there is an inconvenience that even if the capillary column can be produced, it is difficult to form the stationary phase uniformly because the boundary of the partition wall and the spacer on the inner surface of the capillary column is right-angled.

SUMMARY OF THE INVENTION

Therefore, an object of the present invention is to provide a capillary column which can have both high resolution and high sample load capacity without having a rectangular cross section.

In order to achieve such an object, the present invention provides a capillary column comprising a stationary phase on an inactivated inner surface, which is used in gas chromatography, the capillary column comprising: a narrow part formed in a central part of a cross section of internal space and a bulge part formed on each of both sides of the narrow part.

According to the capillary column of the present invention, a generally flat shape can be obtained by forming the cross section of internal space into the shape as described above, and high resolution can be obtained without forming the cross section into a rectangular shape. Further, the capillary column of the present invention can obtain high sample load capacity relative to the circular capillary column having an inside diameter corresponding to the maximum width of the inside dimension of the bulge part. Further, according to the capillary column of the present invention, a long capillary column can be easily produced by forming the cross section of internal space into the shape as described above, and since a continuous curve forms the shape of the cross section, the capillary column has a uniform stationary phase.

Here, in the capillary column according to the present invention, the values of $d_1$, $d_2$, and L are preferably adjusted such that the theoretical plate number is in the range of 1000 to 3000 plates/m (p/m), wherein $d_1$ represents the minimum width of the inside dimension of the narrow part; $d_2$ represents the maximum width of the inside dimension of the bulge part; and L represents the maximum width of the inside dimension in the direction from one bulge part to the other bulge part through the narrow part. A theoretical plate number of less than 1000 plates/m (p/m) may be unable to provide sufficient resolution. Further, it is technically difficult that the theoretical plate number exceeds 3000 plates/m (p/m) in the capillary column of the present invention in which the cross section of internal space has the above shape.

In the capillary column of the present invention, specific values of the above $d_1$, $d_2$, and L are preferably as follows: $d_1$ is in the range of 0.1 to 0.3 mm, $d_2$ is in the range of 0.1 to 0.3 mm; L is in the range of 0.7 to 2 mm; $d_2/d_1$ is in the range of 1 to 3; and $L/d_1$ is in the range of 6 to 20. The capillary column of the present invention can reliably have a theoretical plate number in the range of 1000 to 3000 plates/m (p/m) by setting $d_1$, $d_2$, L, $d_2/d_1$, and $L/d_1$ in the above ranges.

If $d_1$ exceeds 0.3 mm, $d_2$ exceeds 0.3 mm, L exceeds 2 mm, $d_2/d_1$ exceeds 3, or $L/d_1$ exceeds 20, the theoretical plate number of the capillary column of the present invention may be less than 1000 plates/m (p/m). Further, it is technically difficult that $d_1$ is less than 0.1 mm, $d_2$ is less than 0.1 mm, L is less than 0.7 mm, $d_2/d_1$ is less than 1, or $L/d_1$ is less than 6, in the capillary column of the present invention in which the cross section of internal space has the above shape.

A capillary column made of a fused silica tube or a metal tube can be used as the capillary column of the present invention. Examples of metal constituting the metal tube include stainless steel and nickel. Here, when the capillary column of the present invention is made of the metal tube, a capillary column including the stationary phase on an inert thin film coating layer formed on the inner surface of the metal tube can be used.

The capillary column of the present invention made of the metal tube can be produced, for example, by rolling and squeezing a circular capillary column and forming a cross section comprising the narrow part and the bulge part. In the circular capillary column, the inert thin film coating layer is formed on the inner surface of a metal tube having a circular cross section. However, in this case, the inert thin film coating layer which has been previously formed may be damaged by the rolling to form an active site.

Therefore, in the capillary column of the present invention, the capillary column is preferably prepared by rolling a metal tube having a circular cross section, forming the inert thin film coating layer on the inner surface of the metal tube, and then applying a material which forms the stationary phase on the inert thin film coating layer followed by drying. In this way, excellent analysis performance can be obtained without the formation of the active site.

DETAILED DESCRIPTION OF THE PREFERRED EMBODIMENTS

Next, the embodiments of the present invention will be described in more detail with reference to the attached drawings.

Figure 1:
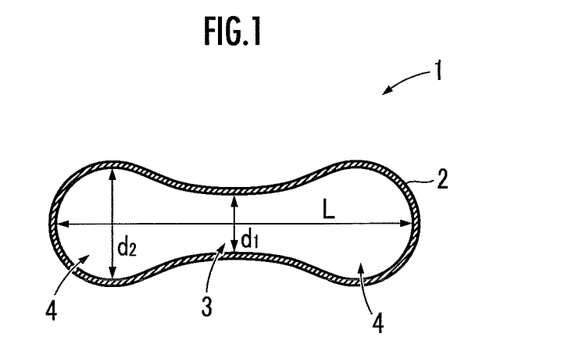
FIG. 1 is a schematic sectional view showing a structure of a capillary column of the present invention.

As schematically shown in FIG. 1, a capillary column 1 of the present embodiment comprises a narrow part 3 formed in the central part of the cross section of the internal space of a stainless steel tube 2 and a bulge part 4 formed on each of both sides of the narrow part 3. The stainless steel tube 2 is inactivated by forming, on the inner surface, an inert thin film coating layer (not shown) made of Si or $SiO_2$ and comprises a stationary phase (not shown) having a thickness of from 0.01 to several micrometers containing, for example, polydimethylsiloxane on the inert thin film coating layer.

Further, in the capillary column 1, the values of $d_1$, $d_2$, and L are adjusted such that the theoretical plate number is in the range of 1000 to 3000 plates/m (p/m), when $d_1$ represents the minimum width of the inside dimension of the narrow part 3; $d_2$ represents the maximum width of the inside dimension of the bulge part 4; and L represents the maximum width of the inside dimension in the direction from one bulge part 4 to the other bulge part 4 through the narrow part 3. Here, the values of $d_1$, $d_2$, and L are as follows: $d_1$ is in the range of 0.1 to 0.3 mm, $d_2$ is in the range of 0.1 to 0.3 mm; L is in the range of 0.7 to 2 mm, $d_2/d_1$ is in the range of 1 to 3; and $L/d_1$ is in the range of 6 to 20.

Note that, in the present application, the terminology of the narrow part and bulge part is used for convenience in the typical shape of the cross section, and the shape of the cross section also includes an ellipse in which $d_1=d_2$.

The capillary column 1 can obtain high resolution because it has a theoretical plate number equivalent to a circular capillary column having an inside diameter corresponding to $d_1$ or $d_2$ in the range as described above. Further, the capillary column 1 can obtain high sample load capacity relative to a circular capillary column having an inside diameter corresponding to $d_2$ by setting $d_1$, $d_2$, L, $d_2/d_1$, and $L/d_1$ to the above range.

Figure 2:
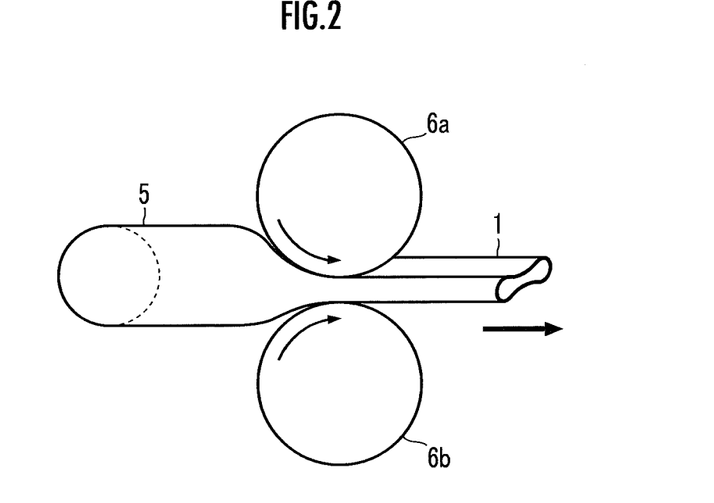
FIG. 2 is a perspective view showing a method for producing a capillary column of the present invention.

The capillary column 1 can be produced by inserting a circular capillary column 5 between a pair of rollers 6a and 6b, as shown in FIG. 2, to thereby roll and squeeze to form a cross section comprising the narrow part 3 and the bulge part 4. The circular capillary column 5 is constituted by a metal tube made of metal such as stainless steel and nickel, and has a circular cross section, and the inert thin film coating layer and the stationary phase are formed in the inner surface of the metal tube.

However, when the circular capillary column 5 is rolled as described above, the inert thin film coating layer previously formed may be damaged by the rolling to form an active site. As a result, when gas chromatography is performed using the capillary column 1 formed, a part of polar components among separated components may be adsorbed to the active site and may not be detected.

Therefore, it is preferred to insert a metal tube having a circular cross section in which the inert thin film coating layer and the stationary phase are not formed in the inner surface thereof between the rollers 6a and 6b instead of the circular capillary column 5 in FIG. 2 to thereby roll the metal tube to form a cross section comprising the narrow part 3 and the bulge part 4. Then, the capillary column 1 can be obtained by forming the inert thin film coating layer and the stationary phase on the inner surface of the metal tube in which the cross section is formed. Since the capillary column 1 obtained in this way does not have a possibility that the active site may be formed therein, none of the separated components will be adsorbed to the active site when gas chromatography is performed, thus capable of obtaining excellent analysis performance.

Next, Examples and Examples of the present invention will be shown.

Example 1

In this Example, a stainless steel tube having an inside diameter of 1.2 mm was used instead of a circular capillary column 5 in FIG. 2, and the stainless steel tube was rolled so as to obtain a $d_1$ of 0.12 mm to thereby form a narrow part 3 and a bulge part 4 in the cross section. An inert thin film coating layer is not formed on the inner surface of the stainless steel tube, and the stationary phase is not formed, either.

Next, an inert thin film coating layer made of $SiO_2$ and a stationary phase made of polydimethylsiloxane were formed on the inner surface of the stainless steel tube in which the narrow part 3 and the bulge part 4 were formed to obtain a capillary column 1.

In the capillary column 1 obtained in this Example, $d_1$ was 0.12 mm, $d_2$ was 0.18 mm, L was 1.72 mm, $d_2/d_1$ was 1.5, and $L/d_1$ was 14.33.

Next, gas chromatography was performed using the capillary column 1 of this Example by using a solution prepared by dissolving a plurality of organic compounds in hexane as a sample. The sample contains undecane, tridecane, tetradecane, and pentadecane as a saturated hydrocarbon compound, 1-decanol as an alcohol compound, 4-chlorophenol as a phenol compound, 1-decyl amine as an amine compound, acenaphthylene as an aromatic compound, and methyl caprate as an ester compound, each in a concentration of about 500 ppm. The gas chromatography was performed using a column having a length of 20 m in a temperature controlled bath at a temperature of 140° C. and by passing helium at a flow rate of 3.0 ml/min as a carrier gas. At this time, the optimum linear velocity was 20.2 cm/s, and the theoretical plate number was 2775 plates/m (p/m) for a component having a distribution ratio of 4.82.

Next, the sample load capacity of the capillary column 1 obtained in this Example was calculated. The sample load capacity was calculated by setting $d_2$ of the capillary column 1 of this Example to approximately 0.25 mm, defining the sample load capacity of a circular capillary column 5 having an inside diameter of 0.25 mm as 1.0, and comparing the sample load capacity of the capillary column 1 of this Example with the sample load capacity of the circular capillary column 5. As a result, the capillary column 1 of this Example had a sample load capacity of 27.6 relative to the circular capillary column 5 having an inside diameter of 0.25 mm.

Figure 3:
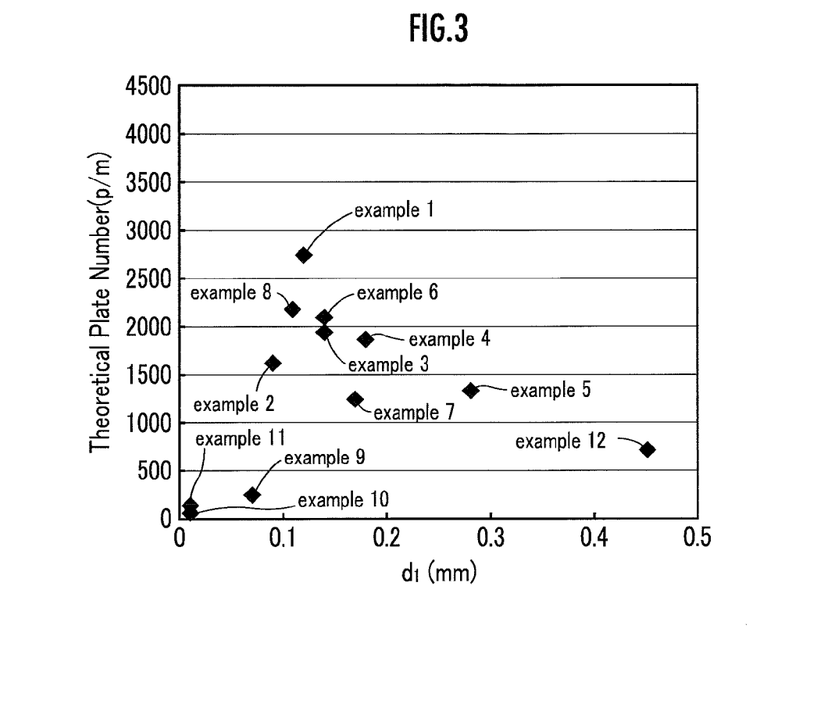
FIG. 3 is a graph showing the relation between $d_1$ and theoretical plate number.
Figure 4:
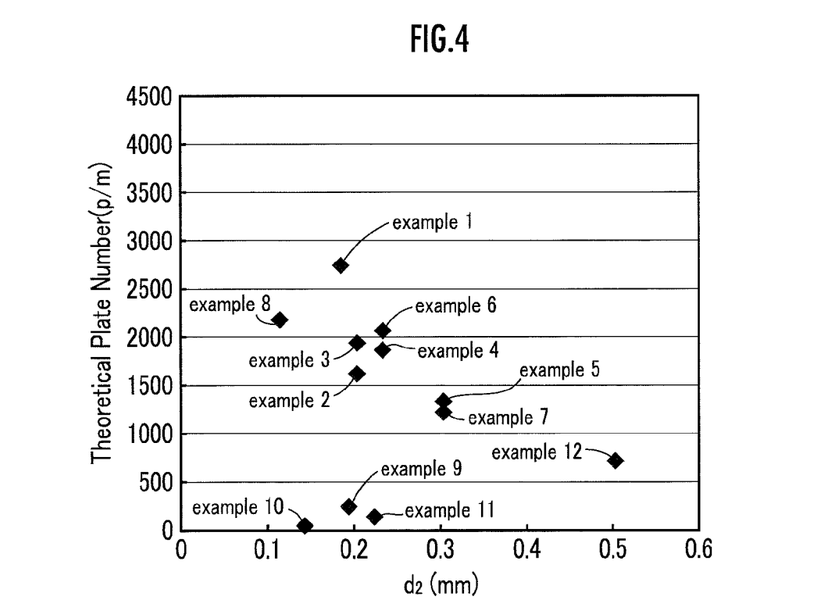
FIG. 4 is a graph showing the relation between $d_2$ and theoretical plate number.
Figure 5:
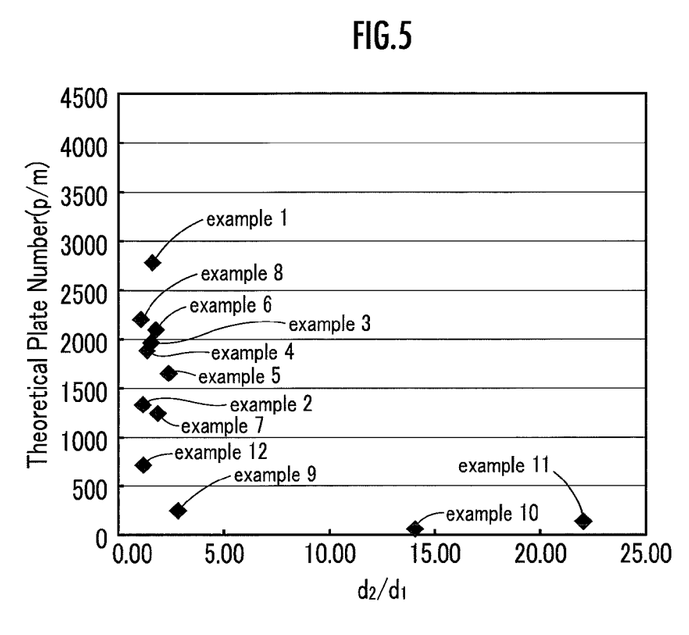
FIG. 5 is a graph showing the relation between $d_2/d_1$ and theoretical plate number.
Figure 6:
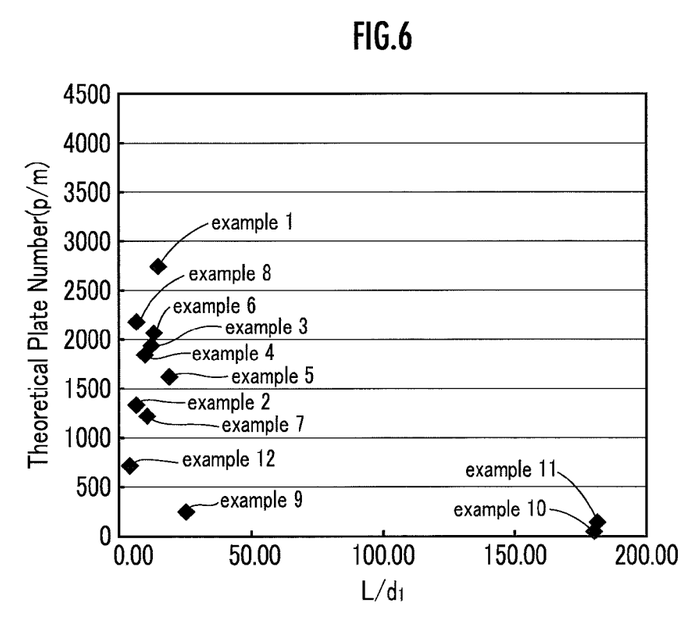
FIG. 6 is a graph showing the relation between $L/d_1$ and theoretical plate number.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Figure 7:
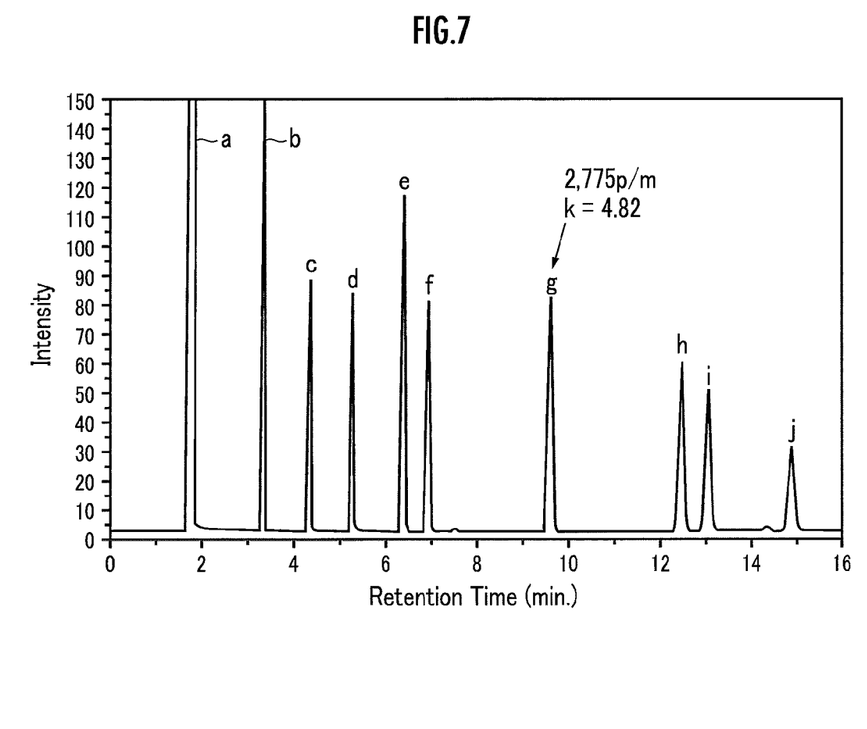
FIG. 7 is a chromatogram showing an example of the results when the capillary column of Example 1 is used in gas chromatography.

Further, FIG. 7 shows the chromatogram obtained in the gas chromatography. In FIG. 7, peak a represents hexane; peak b represents undecane; peak c represents 4-chlorophenol; peak d represents 1-decyl amine; peak e represents tridecane; peak f represents methyl caprate; peak g represents tetradecane; peak h represents acenaphthylene; peak i represents 1-decanol; and peak j represents pentadecane.

Example 2

In this Example, a capillary column 1 was obtained in exactly the same manner as in Example 1 except that a stainless steel tube having an inside diameter of 1.2 mm was rolled so as to obtain a $d_1$ of 0.1 mm. In the capillary column 1 of this Example, $d_1$ was 0.1 mm, $d_2$ was 0.20 mm, L was 1.72 mm, $d_2/d_1$ was 2.0, and $L/d_1$ was 17.2.

Next, gas chromatography was performed in exactly the same manner as in Example 1 except that the capillary column 1 of this Example was used. At this time, the optimum linear velocity was 20.8 cm/s, and the theoretical plate number was 1650 plates/m (p/m) for a component having a distribution ratio of 5.0.

Next, the sample load capacity of the capillary column 1 obtained in this Example was calculated in exactly the same manner as in Example 1. As a result, the capillary column 1 of this Example had a sample load capacity of 35.8 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Figure 8:
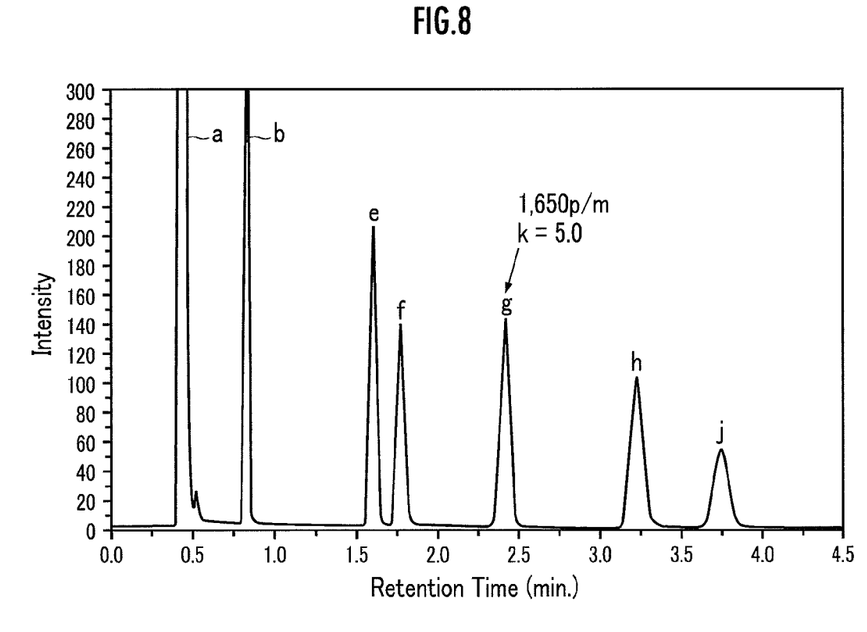
FIG. 8 is a chromatogram showing an example of the results when the capillary column of Example 2 is used in gas chromatography.

Further, FIG. 8 shows the chromatogram obtained in the gas chromatography. In FIG. 8, peaks a, b, e, f, g, h, and j each show the same compound as in FIG. 7.

Example 3

In this Example, a capillary column 1 was obtained in exactly the same manner as in Example 1 except that a stainless steel tube having an inside diameter of 1.2 mm was rolled so as to obtain a $d_1$ of 0.14 mm. In the capillary column 1 of this Example, $d_1$ was 0.14 mm, $d_2$ was 0.20 mm, L was 1.7 mm, $d_2/d_1$ was 1.43, and $L/d_1$ was 12.14.

Next, gas chromatography was performed in exactly the same manner as in Example 1 except that the capillary column 1 of this Example was used. At this time, the optimum linear velocity was 20.3 cm/s, and the theoretical plate number was 1970 plates/m (p/m) for a component having a distribution ratio of 4.56.

Next, the sample load capacity of the capillary column 1 obtained in this Example was calculated in exactly the same manner as in Example 1. As a result, the capillary column 1 of this Example had a sample load capacity of 32.8 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Figure 9:
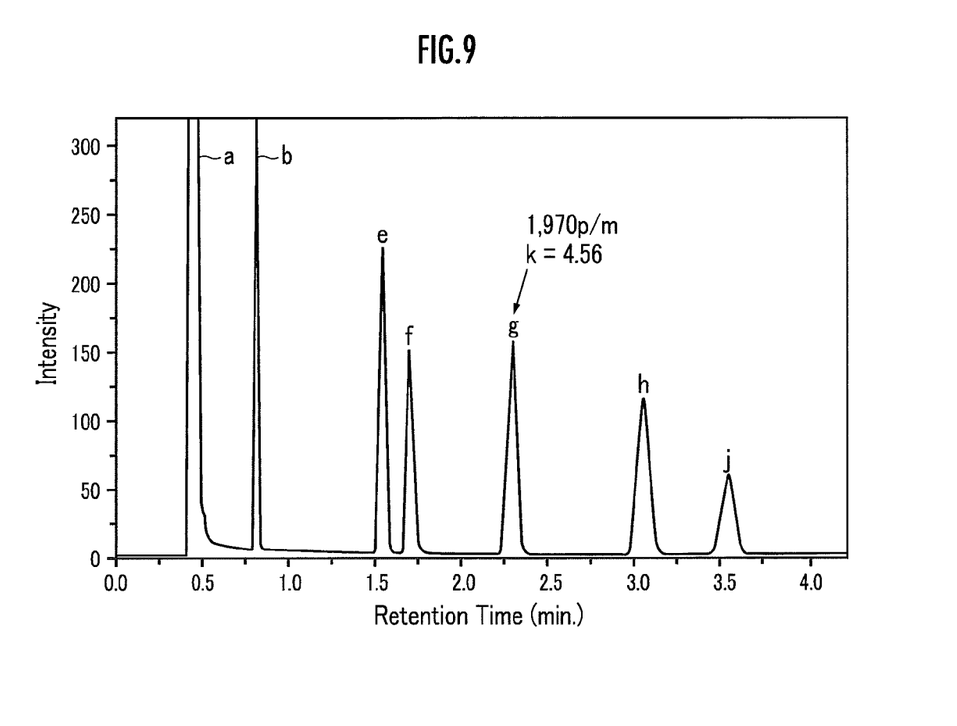
FIG. 9 is a chromatogram showing an example of the results when the capillary column of Example 3 is used in gas chromatography.

Further, FIG. 9 shows the chromatogram obtained in the gas chromatography. In FIG. 9, peaks a, b, e, f, g, h, and j each show the same compound as in FIG. 7.

Example 4

In this Example, a capillary column 1 was obtained in exactly the same manner as in Example 1 except that a stainless steel tube having an inside diameter of 1.2 mm was rolled so as to obtain a $d_1$ of 0.18 mm. In the capillary column 1 of this Example, $d_1$ was 0.18 mm, $d_2$ was 0.23 mm, L was 1.7 mm, $d_2/d_1$ was 1.28, and $L/d_1$ was 79.44.

Next, gas chromatography was performed in exactly the same manner as in Example 1 except that the capillary column 1 of this Example was used. At this time, the optimum linear velocity was 18.1 cm/s, and the theoretical plate number was 1885 plates/m (p/m) for a component having a distribution ratio of 4.23.

Next, the sample load capacity of the capillary column 1 obtained in this Example was calculated in exactly the same manner as in Example 1. As a result, the capillary column 1 of this Example had a sample load capacity of 33.5 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Figure 10:
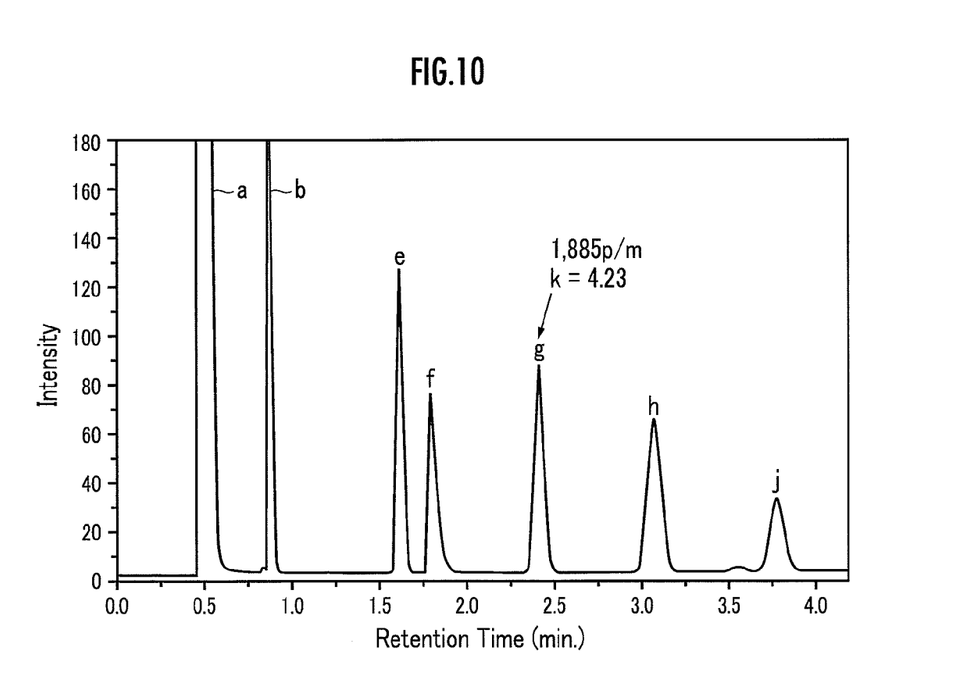
FIG. 10 is a chromatogram showing an example of the results when the capillary column of Example 4 is used in gas chromatography.

Further, FIG. 10 shows the chromatogram obtained in the gas chromatography. In FIG. 10, peaks a, b, e, f, g, h, and j each show the same compound as in FIG. 7.

Example 5

In this Example, a capillary column 1 was obtained in exactly the same manner as in Example 1 except that a stainless steel tube having an inside diameter of 1.2 mm was rolled so as to obtain a $d_1$ of 0.28 mm. In the capillary column 1 of this Example, $d_1$ was 0.28 mm, $d_2$ was 0.30 mm, L was 1.75 mm, $d_2/d_1$ was 1.07, and $L/d_1$ was 6.25.

Next, gas chromatography was performed in exactly the same manner as in Example 1 except that the capillary column 1 of this Example was used. At this time, the optimum linear velocity was 18.9 cm/s, and the theoretical plate number was 1352 plates/m (p/m) for a component having a distribution ratio of 4.05.

Next, the sample load capacity of the capillary column 1 obtained in this Example was calculated in exactly the same manner as in Example 1. As a result, the capillary column 1 of this Example had a sample load capacity of 39.6 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Figure 11:
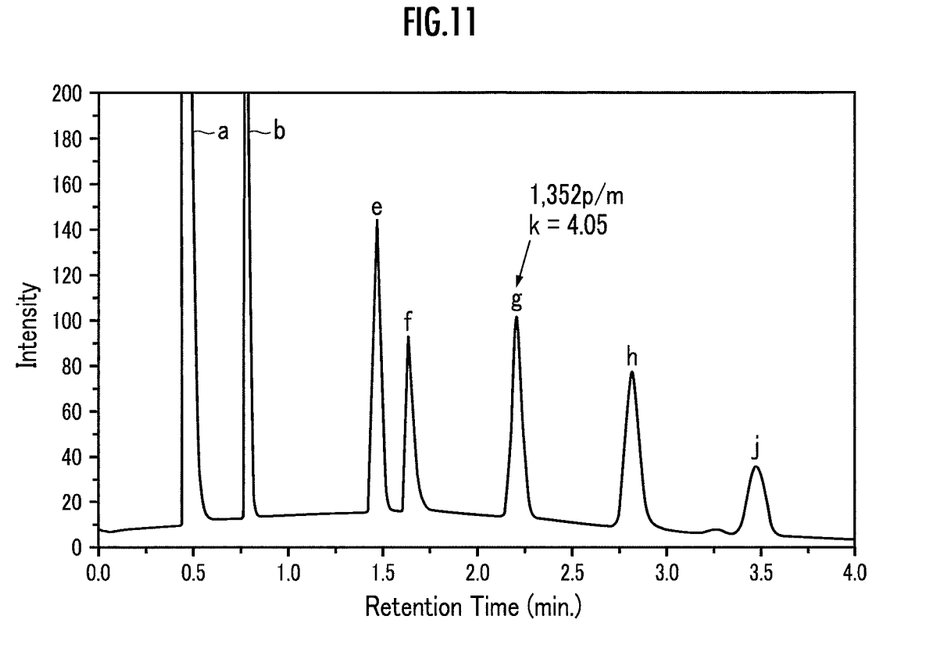
FIG. 11 is a chromatogram showing an example of the results when the capillary column of Example 5 is used in gas chromatography.

Further, FIG. 11 shows the chromatogram obtained in the gas chromatography. In FIG. 11, peaks a, b, e, f, g, h, and j each show the same compound as in FIG. 7.

Example 6

In this Example, a capillary column 1 was obtained in exactly the same manner as in Example 1 except that a stainless steel tube was rolled so as to obtain a $d_1$ of 0.14 mm. In the capillary column 1 of this Example, $d_1$ was 0.14 mm, $d_2$ was 0.23 mm, L was 1.74 mm, $d_2/d_1$ was 1.64, and $L/d_1$ was 12.43.

Next, gas chromatography was performed in exactly the same manner as in Example 1 except that the capillary column 1 of this Example was used. At this time, the theoretical plate number at the optimum linear velocity was 2100 plates/m (p/m).

Next, the sample load capacity of the capillary column 1 obtained in this Example was calculated in exactly the same manner as in Example 1. As a result, the capillary column 1 of this Example had a sample load capacity of 31.7 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Example 7

In this Example, a capillary column 1 was obtained in exactly the same manner as in Example 1 except that a stainless steel tube having an inside diameter of 0.5 mm was rolled so as to obtain a $d_1$ of 0.17 mm. In the capillary column 1 of this Example, $d_1$ was 0.17 mm, $d_2$ was 0.30 mm, L was 1.74 mm, $d_2/d_1$ was 1.76, and $L/d_1$ was 10.24.

Next, gas chromatography was performed in exactly the same manner as in Example 1 except that the capillary column 1 of this Example was used. At this time, the theoretical plate number at the optimum linear velocity was 1263 plates/m (p/m).

Next, the sample load capacity of the capillary column 1 obtained in this Example was calculated in exactly the same manner as in Example 1. As a result, the capillary column 1 of this Example had a sample load capacity of 5.0 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Example 8

In this Example, a capillary column 1 was obtained in exactly the same manner as in Example 1 except that a stainless steel tube having an inside diameter of 0.5 mm was rolled so as to obtain a $d_1$ of 0.11 mm. In the capillary column 1 of this Example, $d_1$ was 0.11 mm, $d_2$ was 0.11 mm, L was 1.71 mm, $d_2/d_1$ was 1.00, and $L/d_1$ was 6.54.

Next, gas chromatography was performed in exactly the same manner as in Example 1 except that the capillary column 1 of this Example was used. At this time, the theoretical plate number at the optimum linear velocity was 2200 plates/m (p/m).

Next, the sample load capacity of the capillary column 1 obtained in this Example was calculated in exactly the same manner as in Example 1. As a result, the capillary column 1 of this Example had a sample load capacity of 3.8 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Example 9

In this Example, a capillary column 1 was obtained in exactly the same manner as in Example 1 except that a stainless steel tube having an inside diameter of 1.2 mm was rolled so as to obtain a $d_1$ of 0.07 mm. In the capillary column 1 of this Example, $d_1$ was 0.07 mm, $d_2$ was 0.19 mm, L was 1.73 mm, $d_2/d_1$ was 2.71, and $L/d_1$ was 24.71.

Next, gas chromatography was performed in exactly the same manner as in Example 1 except that the capillary column 1 of this Example was used. At this time, the theoretical plate number at the optimum linear velocity was 266 plates/m (p/m).

Next, the sample load capacity of the capillary column 1 obtained in this Example was calculated in exactly the same manner as in Example 1. As a result, the capillary column 1 of this Example had a sample load capacity of 89.2 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Example 10

In this Example, a capillary column 1 was obtained in exactly the same manner as in Example 1 except that a stainless steel tube having an inside diameter of 1.2 mm was rolled so as to obtain a $d_1$ of 0.01 mm. In the capillary column 1 of this Example, $d_1$ was 0.01 mm, $d_2$ was 0.14 mm, L was 1.79 mm, $d_2/d_1$ was 14.0, and $L/d_1$ was 179.0.

Next, gas chromatography was performed in exactly the same manner as in Example 1 except that the capillary column 1 of this Example was used. At this time, the theoretical plate number at the optimum linear velocity was 87 plates/m (p/m).

Next, the sample load capacity of the capillary column 1 obtained in this Example was calculated in exactly the same manner as in Example 1. As a result, the capillary column 1 of this Example had a sample load capacity of 156.2 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Example 11

In this Example, a capillary column 1 was obtained in exactly the same manner as in Example 1 except that a stainless steel tube having an inside diameter of 1.2 mm was rolled so as to obtain a $d_1$ of 0.01 mm. In the capillary column 1 of this Example, $d_1$ was 0.01 mm, $d_2$ was 0.22 mm, L was 1.80 mm, $d_2/d_1$ was 22.0, and $L/d_1$ was 180.0.

Next, gas chromatography was performed in exactly the same manner as in Example 1 except that the capillary column 1 of this Example was used. At this time, the theoretical plate number at the optimum linear velocity was 150 plates/m (p/m).

Next, the sample load capacity of the capillary column 1 obtained in this Example was calculated in exactly the same manner as in Example 1. As a result, the capillary column 1 of this Example had a sample load capacity of 118.8 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

Example 12

In this Example, a capillary column 1 was obtained in exactly the same manner as in Example 1 except that a stainless steel tube having an inside diameter of 1.2 mm was rolled so as to obtain a $d_1$ of 0.45 mm. In the capillary column 1 of this Example, $d_1$ was 0.45 mm, $d_2$ was 0.50 mm, L was 1.44 mm, $d_2/d_1$ was 1.11, and $L/d_1$ was 3.20.

Next, gas chromatography was performed in exactly the same manner as in Example 1 except that the capillary column 1 of this Example was used. At this time, the theoretical plate number at the optimum linear velocity was 750 plates/m (p/m).

Next, the sample load capacity of the capillary column 1 obtained in this Example was calculated in exactly the same manner as in Example 1. As a result, the capillary column 1 of this Example had a sample load capacity of 53.1 relative to the circular capillary column 5 having an inside diameter of 0.25 mm.

Table 1 shows $d_1$, $d_2$, L, $d_2/d_1$, $L/d_1$, theoretical plate number, and sample load capacity of the capillary column 1 obtained in this Example. Further, FIG. 3 shows the relation between $d_1$ and theoretical plate number; FIG. 4 shows the relation between $d_2$ and theoretical plate number; FIG. 5 shows the relation between $d_2/d_1$ and theoretical plate number; and FIG. 6 shows the relation between $L/d_1$ and theoretical plate number.

TABLE 1

| | $d_1$ (mm) | $d_2$ (mm) | L (mm) | $d_1/d_2$ | $L/d_1$ | Theoretical plate number (p/m) | Sample load capacity |
|---|---|---|---|---|---|---|---|
| Example 1 | 0.12 | 0.18 | 1.72 | 1.5 | 14.33 | 2775 | 27.6 |
| Example 2 | 0.1 | 0.2 | 1.72 | 2.0 | 17.2 | 1650 | 35.8 |
| Example 3 | 0.14 | 0.20 | 1.7 | 1.43 | 12.14 | 1970 | 32.8 |
| Example 4 | 0.18 | 0.23 | 1.7 | 1.28 | 9.44 | 1885 | 33.5 |
| Example 5 | 0.28 | 0.30 | 1.75 | 1.07 | 6.25 | 1352 | 39.6 |
| Example 6 | 0.14 | 0.23 | 1.74 | 1.64 | 12.43 | 2100 | 31.7 |
| Example 7 | 0.17 | 0.30 | 1.74 | 1.76 | 10.24 | 1263 | 5.0 |
| Example 8 | 0.11 | 0.11 | 1.71 | 1.0 | 6.54 | 2200 | 3.8 |
| Example 9 | 0.07 | 0.19 | 1.73 | 2.71 | 24.71 | 266 | 89.2 |
| Example 10 | 0.01 | 0.14 | 1.79 | 14.0 | 179.0 | 87 | 156.2 |
| Example 11 | 0.01 | 0.22 | 1.80 | 22.0 | 180.0 | 150 | 118.8 |
| Example 12 | 0.45 | 0.50 | 1.44 | 1.11 | 3.20 | 750 | 53.1 |

Sample load capacity: represented by the ratio to the sample load capacity of a circular capillary column having an inside diameter of 0.25 mm, when the sample load capacity of the circular capillary column is defined as 1.0. An index of the detection sensitivity of minor components.

As shown in Table 1 and FIGS. 3 to 6, the capillary columns 1 of Examples 1 to 8 can have a theoretical plate number at the optimum linear velocity in the range of 1263 to 2775 plates/m (p/m) because $d_1$ is in the range of 0.1 to 0.3 mm, $d_2$ is in the range of 0.1 to 0.3 mm, L is in the range of 0.7 to 2 mm, $d_2/d_1$ is in the range of 1 to 3, and $L/d_1$ is in the range of 6 to 20. Further, as described above, the capillary columns 1 of Examples 1 to 8 can obtain a sample load capacity in the range of 3.8 to 39.6 when the sample load capacity of the circular capillary column 5 having an inside diameter of 0.25 mm is defined as 1.0. Therefore, it is obvious that the capillary columns 1 of Examples 1 to 8 can have both high resolution and high sample load capacity.

In contrast to the capillary columns 1 of Examples 1 to 8, the capillary columns 1 of Examples 9 to 11 in which $d_1$ is less than 0.1 mm has high sample load capacity in the range of 89.2 to 156.0, but on the other hand it has a theoretical plate number at the optimum linear velocity in the range of 87 to 266 plates/m (p/m), thus being unable to obtain sufficient resolution.

Further, in contrast to the capillary columns 1 of Examples 1 to 8, the capillary column 1 of Example 12 in which $d_1$ exceeds 0.3 mm has high sample load capacity of 53.1, but on the other hand it has a theoretical plate number at the optimum linear velocity of 750 plates/m (p/m), thus being unable to obtain sufficient resolution.

What is claimed is:

1. A capillary column configured to have a stationary phase on an inactivated inner surface, which is used in gas chromatography, the capillary column comprising:

a narrow part formed in a central part of a cross section of an internal space and a bulge part formed on each of both sides in a longitudinal direction of the narrow part, wherein the bulge part bulges outwardly in a transverse direction compared with the narrow part;

wherein values of $d_1$, $d_2$, and L are adjusted such that a theoretical plate number is in a range of 1000 to 3000 plates/m, wherein $d_1$ represents a minimum width of an inside dimension of the narrow part in the transverse direction; $d_2$ represents a maximum width of the inside dimension of the bulge part in the transverse direction; and L represents a maximum width of the inside dimension in the longitudinal direction from one bulge part to the other bulge part through the narrow part; and wherein $d_2$ is greater than $d_1$; $d_1$ is in a range of 0.1 to 0.3 mm; $d_2$ is in a range of 0.1 to 0.3 mm, L is in a range of 0.7 to 2 mm; $d_2/d_1$ is in a range of more than 1 to 3; and $L/d_1$ is in a range of 6 to 20.

2. The capillary column according to claim 1, wherein the capillary column is constituted by a metal tube and is configured to have the stationary phase on an inert thin film coating layer formed on the inner surface of the metal tube.

3. The capillary column according to claim 2, wherein the capillary column is prepared by rolling a metal tube having a circular cross section, forming the inert thin film coating layer on the inner surface of the metal tube, and thereafter applying a material which forms the stationary phase on the inert thin film coating layer followed by drying.

4. The capillary column according to claim 2, wherein the metal tube is made of stainless steel or nickel.

5. The capillary column according to claim 2, wherein the inert thin film coating layer is made of Si or $SiO_2$.

6. The capillary column according to claim 2, wherein the stationary phase is made of polydimethylsiloxane.

7. The capillary column according to claim 2, wherein the capillary column comprises a rolled metal tube, which prior to rolling thereof had a circular cross section, and further comprises the inert thin film coating layer formed on the inner surface of the rolled metal tube, and a material that forms the stationary phase deposited and dried on the inert thin film coating layer.

* * * * *